(12) United States Patent
Nichols

(10) Patent No.: US 12,131,810 B2
(45) Date of Patent: Oct. 29, 2024

(54) AUTOMATED CODE FEEDBACK SYSTEM

(71) Applicant: Solventum Intellectual Properties Company, Maplewood, MN (US)

(72) Inventor: Derek L. Nichols, Douglasville, GA (US)

(73) Assignee: Solventum Intellectual Properties Company, Maplewood, MN (US)

( * ) Notice: Subject to any disclaimer, the term of this patent is extended or adjusted under 35 U.S.C. 154(b) by 0 days.

(21) Appl. No.: 17/651,613

(22) Filed: Feb. 18, 2022

(65) Prior Publication Data

US 2022/0172810 A1   Jun. 2, 2022

Related U.S. Application Data

(63) Continuation of application No. 16/193,443, filed on Nov. 16, 2018, now Pat. No. 11,282,596.
(Continued)

(51) Int. Cl.
*G16H 15/00* (2018.01)
*G06F 40/274* (2020.01)
(Continued)

(52) U.S. Cl.
CPC .......... *G16H 15/00* (2018.01); *G06F 40/274* (2020.01); *G06F 40/35* (2020.01); *G10L 15/18* (2013.01); *G10L 15/22* (2013.01); *G10L 15/26* (2013.01)

(58) Field of Classification Search
CPC .......... G10L 15/18; G10L 15/22; G10L 15/26; G16H 15/00; G16H 10/60; G16H 10/20; G16H 50/20; G16H 50/70; G16H 40/67; G06F 40/274; G06F 40/35; G06F 19/322; G06F 19/345; G06Q 10/10; G06Q 10/06; G06Q 40/08
(Continued)

(56) References Cited

U.S. PATENT DOCUMENTS

| 2,233,938 A | 3/1941 | Jones |
| 3,006,183 A | 10/1961 | Baker |

(Continued)

FOREIGN PATENT DOCUMENTS

| EP | 1571608 A2 | 9/2005 |
| EP | 1361522 B1 | 8/2011 |

(Continued)

OTHER PUBLICATIONS

"Medical transcription—Wikipedia", Feb. 13, 2010, Retrieved from the Internet on Sep. 6, 2022], URL: <https://en.wikipedia.org/w/index.php?title=Medical_transcription&oldid=343657066>, 9 pages.
(Continued)

*Primary Examiner* — Leshui Zhang

(57) ABSTRACT

A computer system automatically generates and provides real-time feedback to a healthcare provider about a selected Evaluation and Management (E/M) level to assign to a patient encounter. The system provides the feedback while the healthcare provider is creating the clinical note that documents the patient encounter. The system may also automatically generate and suggest E/M levels to the healthcare provider for approval by the healthcare provider while the healthcare provider is creating the clinical note.

17 Claims, 2 Drawing Sheets

Related U.S. Application Data

(60) Provisional application No. 62/590,114, filed on Nov. 22, 2017.

(51) Int. Cl.
| | |
|---|---|
| *G06F 40/35* | (2020.01) |
| *G10L 15/18* | (2013.01) |
| *G10L 15/22* | (2006.01) |
| *G10L 15/26* | (2006.01) |

(58) Field of Classification Search
USPC ....... 704/235, 231, 232, 233, 237, 238, 239, 704/240, 245, 246, 251; 706/924, 10, 20, 706/21
See application file for complete search history.

(56) References Cited

U.S. PATENT DOCUMENTS

| | | | |
|---|---|---|---|
| 3,024,196 A | 3/1962 | Eckert | |
| 3,082,310 A | 3/1963 | Sakamoto | |
| 3,182,039 A | 5/1965 | Remy | |
| 3,275,643 A | 9/1966 | Lubowe | |
| 3,311,854 A | 3/1967 | Mason | |
| 3,345,249 A | 10/1967 | Stephan | |
| 3,377,922 A | 4/1968 | Spender et al. | |
| 3,424,523 A | 1/1969 | Branigan | |
| 3,463,673 A | 8/1969 | Stroup et al. | |
| 3,468,167 A | 9/1969 | Klass et al. | |
| 3,583,439 A | 6/1971 | Dolenz et al. | |
| 3,679,077 A | 7/1972 | Gennick | |
| 3,704,099 A | 11/1972 | Sanz | |
| 3,706,521 A | 12/1972 | Kopelman et al. | |
| 3,738,784 A | 6/1973 | Clark et al. | |
| 3,781,829 A | 12/1973 | Singh | |
| 3,805,703 A | 4/1974 | Cummings | |
| 3,834,264 A | 9/1974 | Moshofsky | |
| 5,065,315 A | 11/1991 | Garcia | |
| 5,148,366 A | 9/1992 | Buchanan et al. | |
| 5,483,443 A | 1/1996 | Milstein et al. | |
| 5,664,109 A | 9/1997 | Johnson et al. | |
| 5,823,948 A | 10/1998 | Ross, Jr. et al. | |
| 7,236,968 B2 | 6/2007 | Seki et al. | |
| 7,313,515 B2 | 12/2007 | Crouch et al. | |
| 7,447,988 B2 | 11/2008 | Ross | |
| 7,519,529 B1 | 4/2009 | Horvitz | |
| 7,584,103 B2 | 9/2009 | Fritsch et al. | |
| 7,613,610 B1 | 11/2009 | Zimmerman et al. | |
| 7,716,040 B2 | 5/2010 | Koll et al. | |
| 7,725,330 B2 | 5/2010 | Rao et al. | |
| 7,869,998 B1 | 1/2011 | Di Fabbrizio et al. | |
| 7,885,811 B2 | 2/2011 | Zimmerman et al. | |
| 8,050,938 B1 | 11/2011 | Green, Jr. et al. | |
| 8,781,829 B2 | 7/2014 | Koll et al. | |
| 8,781,853 B2 | 7/2014 | Green, III et al. | |
| 9,082,310 B2 | 7/2015 | Koll et al. | |
| 10,156,956 B2 | 12/2018 | Koll et al. | |
| 10,325,296 B2 | 6/2019 | Koll et al. | |
| 10,877,620 B2 | 12/2020 | Koll et al. | |
| 10,950,329 B2 | 3/2021 | Koll et al. | |
| 11,043,306 B2 | 6/2021 | El Saadawi | |
| 11,232,402 B2 | 1/2022 | Koll et al. | |
| 2001/0042080 A1 | 11/2001 | Ross | |
| 2002/0029161 A1 | 3/2002 | Brodersen et al. | |
| 2002/0065854 A1 | 5/2002 | Pressly | |
| 2002/0077819 A1 | 6/2002 | Girardo | |
| 2002/0099717 A1 | 7/2002 | Bennett | |
| 2002/0120466 A1 | 8/2002 | Finn | |
| 2002/0198741 A1 | 12/2002 | Randazzo | |
| 2003/0074248 A1 | 4/2003 | Braud et al. | |
| 2003/0133156 A1 | 7/2003 | Cragun et al. | |
| 2003/0154085 A1 | 8/2003 | Kelley | |
| 2003/0181790 A1 | 9/2003 | David et al. | |
| 2004/0044546 A1 | 3/2004 | Moore | |
| 2004/0078215 A1 | 4/2004 | Dahlin et al. | |
| 2004/0128163 A1 | 7/2004 | Goodman et al. | |
| 2004/0172297 A1 | 9/2004 | Rao et al. | |
| 2004/0240720 A1 | 12/2004 | Brantley et al. | |
| 2004/0243545 A1 | 12/2004 | Boone et al. | |
| 2004/0254816 A1 | 12/2004 | Myers | |
| 2005/0071194 A1 | 3/2005 | Bormann et al. | |
| 2005/0102140 A1 | 5/2005 | Davne et al. | |
| 2005/0137910 A1 | 6/2005 | Rao et al. | |
| 2005/0158767 A1 | 7/2005 | Haskell et al. | |
| 2005/0171819 A1 | 8/2005 | Keaton et al. | |
| 2005/0228815 A1 | 10/2005 | Carus et al. | |
| 2005/0240439 A1 | 10/2005 | Covit et al. | |
| 2005/0251422 A1 | 11/2005 | Wolfman et al. | |
| 2005/0273360 A1 | 12/2005 | Drucker et al. | |
| 2006/0020492 A1 | 1/2006 | Cousineau et al. | |
| 2006/0020493 A1* | 1/2006 | Cousineau | G10L 15/1822 705/2 |
| 2006/0020886 A1 | 1/2006 | Agrawal et al. | |
| 2006/0036472 A1 | 2/2006 | Crockett | |
| 2006/0041428 A1 | 2/2006 | Fritsch et al. | |
| 2006/0122865 A1 | 6/2006 | Preiss et al. | |
| 2006/0129435 A1 | 6/2006 | Smitherman et al. | |
| 2006/0277073 A1 | 12/2006 | Heilbrunn et al. | |
| 2007/0013968 A1 | 1/2007 | Ebaugh et al. | |
| 2007/0016450 A1 | 1/2007 | Bhora et al. | |
| 2007/0016451 A1 | 1/2007 | Tilson et al. | |
| 2007/0033073 A1 | 2/2007 | Tajaliawal et al. | |
| 2007/0050187 A1 | 3/2007 | Cox | |
| 2007/0067185 A1 | 3/2007 | Halsted | |
| 2007/0088564 A1 | 4/2007 | March, Jr. et al. | |
| 2007/0106751 A1 | 5/2007 | Moore | |
| 2007/0112599 A1 | 5/2007 | Liu | |
| 2007/0118410 A1 | 5/2007 | Nadai | |
| 2007/0143141 A1 | 6/2007 | Mllasenor et al. | |
| 2007/0192143 A1 | 8/2007 | Krishnan et al. | |
| 2007/0198907 A1 | 8/2007 | Degala et al. | |
| 2007/0203708 A1 | 8/2007 | Polcyn et al. | |
| 2007/0226211 A1 | 9/2007 | Heinze et al. | |
| 2007/0276649 A1 | 11/2007 | Schubert | |
| 2007/0299651 A1 | 12/2007 | Koll et al. | |
| 2007/0299665 A1 | 12/2007 | Koll et al. | |
| 2008/0004505 A1 | 1/2008 | Kapit et al. | |
| 2008/0016164 A1 | 1/2008 | Chandra | |
| 2008/0028300 A1 | 1/2008 | Krieger et al. | |
| 2008/0077451 A1 | 3/2008 | Anthony et al. | |
| 2008/0141117 A1 | 6/2008 | King et al. | |
| 2008/0249374 A1 | 10/2008 | Morita et al. | |
| 2009/0048833 A1 | 2/2009 | Fritsch et al. | |
| 2009/0070290 A1 | 3/2009 | Nye | |
| 2009/0077658 A1 | 3/2009 | King et al. | |
| 2009/0187407 A1 | 7/2009 | Soble et al. | |
| 2009/0192800 A1 | 7/2009 | Brandt | |
| 2009/0192822 A1 | 7/2009 | Regulapati et al. | |
| 2009/0228299 A1 | 9/2009 | Kangarloo et al. | |
| 2009/0271218 A1 | 10/2009 | Mok et al. | |
| 2009/0287678 A1 | 11/2009 | Brown et al. | |
| 2010/0063907 A1 | 3/2010 | Savani et al. | |
| 2010/0094657 A1 | 4/2010 | Stern et al. | |
| 2010/0099974 A1 | 4/2010 | Desai | |
| 2010/0100570 A1 | 4/2010 | Constantin et al. | |
| 2010/0125450 A1 | 5/2010 | Michaelangelo et al. | |
| 2010/0138241 A1 | 6/2010 | Ruark et al. | |
| 2010/0250236 A1 | 9/2010 | Jagannathan et al. | |
| 2010/0278453 A1 | 11/2010 | King | |
| 2010/0299135 A1* | 11/2010 | Fritsch | G06F 40/30 704/E15.044 |
| 2010/0299320 A1 | 11/2010 | Claud et al. | |
| 2011/0043652 A1 | 2/2011 | King et al. | |
| 2011/0055688 A1 | 3/2011 | Isidore | |
| 2011/0239146 A1 | 9/2011 | Dutta et al. | |
| 2011/0295864 A1 | 12/2011 | Betz et al. | |
| 2011/0301978 A1 | 12/2011 | Shiu et al. | |
| 2012/0010900 A1 | 1/2012 | Kaniadakis | |
| 2012/0016690 A1 | 1/2012 | Ramarajan et al. | |
| 2012/0041950 A1 | 2/2012 | Koll et al. | |
| 2012/0065987 A1 | 3/2012 | Farooq et al. | |
| 2012/0166220 A1 | 6/2012 | Baldwin et al. | |
| 2012/0185275 A1 | 7/2012 | Loghmani | |
| 2012/0215551 A1 | 8/2012 | Flanagan et al. | |

(56) References Cited

U.S. PATENT DOCUMENTS

| | | | |
|---|---|---|---|
| 2012/0215782 | A1 | 8/2012 | Jagannathan et al. |
| 2012/0239429 | A1 | 9/2012 | Corfield |
| 2012/0323598 | A1 | 12/2012 | Koll et al. |
| 2013/0144651 | A1 | 6/2013 | Rao |
| 2013/0159408 | A1 | 6/2013 | Winn et al. |
| 2013/0226617 | A1 | 8/2013 | Mok et al. |
| 2013/0238330 | A1 | 9/2013 | Casella Dos Santos |
| 2014/0006431 | A1 | 1/2014 | Jagannathan et al. |
| 2014/0019128 | A1 | 1/2014 | Riskin et al. |
| 2014/0047375 | A1 | 2/2014 | Koll et al. |
| 2014/0108047 | A1 | 4/2014 | Kinney et al. |
| 2014/0164197 | A1* | 6/2014 | Koll .................. G06Q 30/04 705/34 |
| 2014/0278553 | A1 | 9/2014 | Fritsch et al. |
| 2014/0288970 | A1 | 9/2014 | Lee et al. |
| 2014/0324423 | A1 | 10/2014 | Koll et al. |
| 2014/0343963 | A1 | 11/2014 | Fritsch et al. |
| 2015/0088504 | A1 | 3/2015 | Jagannathan et al. |
| 2015/0134349 | A1 | 5/2015 | Vdovjak et al. |
| 2015/0278449 | A1 | 10/2015 | Laborde |
| 2015/0371145 | A1 | 12/2015 | Koll et al. |
| 2016/0147955 | A1 | 5/2016 | Shah |
| 2016/0179770 | A1 | 6/2016 | Koll et al. |
| 2016/0267232 | A1 | 9/2016 | Koll et al. |
| 2016/0294964 | A1 | 10/2016 | Brune et al. |
| 2016/0335554 | A1 | 11/2016 | Koll et al. |
| 2017/0270626 | A1 | 9/2017 | Koll et al. |
| 2018/0040087 | A1 | 2/2018 | Koll et al. |
| 2018/0081859 | A1 | 3/2018 | Snider et al. |
| 2018/0101879 | A1 | 4/2018 | Koll et al. |
| 2018/0276188 | A1 | 9/2018 | Koll et al. |
| 2019/0026436 | A1* | 1/2019 | Bender .................. G06F 16/68 |
| 2019/0065008 | A1 | 2/2019 | Koll et al. |

FOREIGN PATENT DOCUMENTS

| | | | |
|---|---|---|---|
| EP | 2030198 | B1 | 8/2018 |
| EP | 2030196 | B1 | 9/2018 |
| JP | 09106428 | A | 4/1997 |
| JP | 2005267358 | A | 9/2005 |
| JP | 2006509295 | A | 3/2006 |
| JP | 4037250 | B2 | 1/2008 |
| JP | 2008108021 | A | 5/2008 |
| JP | 2009211157 | A | 9/2009 |
| JP | 2011118538 | A | 6/2011 |
| JP | 5986930 | B2 | 9/2016 |
| JP | 6023593 | B2 | 11/2016 |
| JP | 6078057 | B2 | 2/2017 |
| WO | 2005122002 | A2 | 7/2008 |
| WO | 2009143395 | A1 | 11/2009 |
| WO | 2011100474 | A3 | 8/2011 |
| WO | 2011106776 | A2 | 9/2011 |
| WO | 2012048306 | A2 | 4/2012 |
| WO | 2012177611 | A3 | 12/2012 |
| WO | 2014120501 | A2 | 8/2014 |
| WO | 2015079354 | A1 | 6/2015 |
| WO | 2015136404 | A1 | 9/2015 |
| WO | 2015187604 | A1 | 12/2015 |
| WO | 2016149003 | A1 | 9/2016 |
| WO | 2018136417 | A1 | 7/2018 |
| WO | 2019103930 | A1 | 5/2019 |

OTHER PUBLICATIONS

Communication Pursuant to Article 94(3) EPC, mailed Jun. 27, 2019, in EPO application No. 14762803.6, 10 pages.

Daugherty, "Tracking Incidental Findings", Radiology Today, Jul. 2014, vol. 15, No. 7, p. 6.

Decision of Refusal mailed Apr. 19, 2021, by the European Patent Office in patent application No. 13809956.9, 12 pages.

Decision to Refuse European Application mailed Oct. 24, 2019, in European Patent Application No. 11748231.5, 19 pages.

Dimick, "Quality Check: an Overview of Quality Measures and Their Uses", Journal of AHIMA 81, No. 9, Sep. 2010, pp. 34-38, Retrieved from the Internet on Sep. 6, 2022], URL: <http://library.ahima.org/xpedio/groups/public/documents/ahimajDok1_047952.hcsp?DocName=bok1_047952>.

Dutta, "Automated Detection Using Natural Language Processing of Radiologists Recommendations or Additional Imaging of Incidental Findings," Annals of Emergency Medicine, Aug. 2013, vol. 62, No. 2, pp. 162-169.

Examination Report mailed Feb. 4, 2020, in Canadian patent application No. 2,904,656, 5 pages.

Examination Report mailed Jun. 18, 2019, in Canadian patent application No. 2,811,942, 6 pages.

Examination Report received in Canadian patent application No. 2,791,292 on Aug. 2, 2019, 7 pages.

Examination Report received in Canadian patent application No. 2,791,292 on Mar. 9, 2020, 3 pages.

Examiner's Report mailed Jun. 27, 2019, in Canadian Patent Application No. 2,881,564, 6 pages.

Examiner's Report mailed Nov. 29, 2019, in Canadian patent application No. 2,839,266, 4 pages.

Extended European Search Report mailed Jul. 15, 2021, in European patent application No. 18880181.5, 9 pages.

Extended European Search Report mailed Sep. 25, 2020, in European patent application No. 18741689.6, 14 pages.

Final Rejection mailed Jan. 21, 2021, for U.S. Appl. No. 15/993,958 of Detlef Koll, filed May 31, 2018, 21 pages.

Final Rejection mailed Jul. 14, 2020, for U.S. Appl. No. 15/788,522 of Detlef Koll, filed Oct. 19, 2017, 33 pages.

Final Rejection mailed Jul. 21, 2020, in U.S. Appl. No. 15/872,532 of Gilan El Saadawi, filed Jan. 16, 2018, 38 pages.

Final Rejection mailed Mar. 16, 2020, for U.S. Appl. No. 15/993,958 of Detlef Koll, filed May 31, 2018, 33 pages.

Final Rejection mailed Nov. 5, 2019, for U.S. Appl. No. 14/941,445 of Detlef Koll, filed Nov. 13, 2015,19 pages.

Final Rejection mailed Nov. 27, 2019, for U.S. Appl. No. 15/872,532 of Gilan El Saadawi, filed Jan. 16, 2018, 33 pages.

Final Rejection mailed Oct. 29, 2020, for U.S. Appl. No. 15/616,884 of Detlef Koll, filed Jun. 7, 2017, 9 pages.

First Examination Report in Indian patent application No. 2186/MUMNP/2012 on Jul. 19, 2019, 7 pages.

First Examination Report mailed Aug. 29, 2019, in Indian patent application No. 448/MUMNP/2013, 6 pages.

First Examination Report mailed Dec. 24, 2019, in Indian patent application No. 336/DELNP/2014, 7 pages.

First Examination Report mailed Oct. 7, 2019, in Indian patent application No. 7449/DELNP/2012, 9 pages.

Hassanpour, "Information extraction from multi-institutional radiology reports," Artificial Intelligence in Medicine, Jan. 2016, vol. 66, pp. 29-39.

International Preliminary Report on Patentability, mailed Jul. 23, 2019 in International Patent Application No. PCT/US2018/013868, 8 pages.

International Search Report and Written Opinion received for PCT Patent Application No. PCT/US2018/013868, mailed, Jun. 18, 2018, 14 pages.

Matt, Open VPMS, Follow-up tasks, Sep. 17, 2010, Retrieved from the Internet on Sep. 7, 2022, URL: <https://openvpms.org/project/bllowup-task-lists-enhancements>, 3 pages.

Medicare Physician Guide: 1995 Documentation Guidelines for Evaluation and Management Services, Centers for Medicare & Medicaid Services, 1995, Retrieved from the Internet on Sep. 6, 2022, URL: <https://www.cms.gov/Outreach-and-Education/Medicare-Learning-Network-MLN/MLNEdWebGuide/Downloads/95Docguidelines.pdf>, 16 pages.

Medicare Physician Guide: 1997 Documentation Guidelines for Evaluation and Management Services, Centers for Medicare & Medicaid Services, 1997, Retrieved from the Internet on Sep. 6, 2022, URL: <https://www.cms.gov/Outreach-and-Education/Medicare-Learning-Network-MLN/MLNEdWebGuide/Downloads/97Docguidelines.pdf>, 49 pages.

Non-Final Rejection mailed Apr. 1, 2021, for U.S. Appl. No. 15/616,884 of Detlef Koll, filed Jun. 7, 2017, 99 pages.

(56) References Cited

OTHER PUBLICATIONS

Non-Final Rejection mailed Apr. 3, 2020, for U.S. Appl. No. 15/872,532 of Gilan El Saadawi, filed Jan. 16, 2018, 22 pages.
Non-Final Rejection mailed Apr. 6, 2020, for U.S. Appl. No. 15/616,884 of Detlef Koll, filed Jun. 7, 2017, 7 pages.
Non-Final Rejection mailed Jan. 9, 2020 for U.S. Appl. No. 15/788,522 of Detlef Koll, filed Oct. 19, 2017,55 pages.
Non-Final Rejection mailed Jul. 22, 2019, in U.S. Appl. No. 14/941,445 of Detlef Koll, filed Nov. 13, 2015, 29 pages.
Non-Final Rejection mailed Jun. 10, 2020, for U.S. Appl. No. 15/993,958 of Detlef Koll, filed May 31, 2018, 14 pages.
Non-Final Rejection mailed Mar. 6, 2020, in U.S. Appl. No. 14/941,445 of Detlef Koll, filed Nov. 13, 2015, 16 pages.
Non-Final Rejection mailed Mar. 19, 2020, for U.S. Appl. No. 16/174,503 of Detlef Koll, filed Oct. 30, 2018, 43 pages.
Non-Final Rejection mailed Sep. 16, 2019, in U.S. Appl. No. 15/993,958 of Detlef Koll, filed May 31, 2018, 65 pages.
Notice of Allowance mailed Mar. 9, 2021, for U.S. Appl. No. 15/872,532 of Gilan El Saadawi, filed Jan. 16, 2018, 26 pages.
Notice of Allowance mailed Nov. 3, 2020, for U.S. Appl. No. 14/941,445 of Detlef Koll, filed Nov. 6, 13, 2015, 42 pages.
Notice of Allowance mailed Sep. 11, 2020, for U.S. Appl. No. 16/174,503 of Detlef Koll, filed Oct. 30, 2018, 33 pages.
Notice of Allowance mailed Sep. 30, 2021, for U.S. Appl. No. 15/616,884 of Detlef Koll, filed Jun. 17, 2017,25 pages.
Second Examiner's Report mailed May 20, 2020, in Canadian patent application No. 2,875,584, 5 pages.
Sharma, "Context-based Speech Recognition Error Detection and Correction", Proceedings of HLT-NAACL, 2004, Short Papers, May 2004, 4 pages.
Summons to Attend Oral Proceedings Pursuant to Rule 115(1) EPC mailed Mar. 24, 2020, by the European Patent Office in patent application No. 13809956.9, 10 pages.
XPatterns Clinical Auto-Coding, Atigeo, Whitepaper, 2014, 8 pages.
Yetisgen-Yildiz, "A text processing pipeline to extract recommendations from radiology reports," Journal of Biomedical Informatics, Jan. 2013, vol. 46, No. 2, pp. 354-362.
Adam, "ESR guidelines for the communication of urgent and unexpected findings" European Society of Radiology (ESR), Insights into Imaging, 2011, vol. 3, No. 1, pp. 1-3.
Summons to Attend Oral Proceedings Pursuant to Rule 115(1) EPC mailed Jun. 12, 2019 in European Patent application No. 11748231.5, 11 pages.
Third Examiner's Report mailed Apr. 22, 2021, in Canadian patent application No. 2,875,584, 4 pages.

\* cited by examiner

AUTOMATED CODE FEEDBACK SYSTEM

BACKGROUND

When a healthcare provider provides healthcare services to a patient in a patient encounter, the provider must create accurate, precise, and complete clinical documentation in order to provide the patient with high quality care, and in order for the provider to receive proper and timely payment for services rendered. Facts, findings, and observations about the patient's history, current physiological state, treatment options, and need for medical follow-up must be recorded. Physicians and other healthcare providers typically document patient encounters in a clinical note, which may be stored in a document and/or Electronic Medical Record (EMR) system.

As a side-effect of providing patient care, healthcare providers must be paid for the services they provide. The services are reported with codes developed by the American Medical Association (AMA) and published in the Current Procedural Terminology (CPT) with yearly updates to reflect new and emerging medical technology. A specific subsection of CPT, Evaluation and Management (E/M), was established to report provider services that do not involve diagnostic or therapeutic procedures. These services are typically represented in physician office visits, consultative services, or daily inpatient hospital visits, but can include services provided in locations such as emergency rooms, hospice facilities, and nursing homes. According to the Evaluation and Management Service Guidelines as published in the American Medical Association's Current Procedural Technology, "The levels of E/M services encompass the wide variations in skill, effort, time, responsibility, and medical knowledge required for the prevention or diagnosis and treatment of illness or injury and the promotion of optimal health." Low E/M levels represent problem-focused patient encounters with straightforward medical decision making whereas high levels represent comprehensive encounters with medical decision making of high complexity. The documentation of the patient encounter that is created by the healthcare provider is used as the evidentiary record of the service provided in support of an E/M level assigned to the patient encounter.

One set of E/M standards is entitled, "1995 Documentation Guidelines for Evaluation and Management Services," available online at https://www.cms.gov/Outreach-and-Education/Medicaare-Learning-Network-MLN/MLNEdWebGuide/Downloads/95Docguidelines.pdf, and hereby incorporated by reference herein. Another set of E/M standards is entitled, "1997 Documentation Guidelines for Evaluation and Management Services," available online at https://www.cms.gov/Outreach-and-Education/Medicare-Learning-Network-MLN/MLNEdWebGuide/Downloads/97Docquidelines.pdf, and hereby incorporated by reference herein. As described in those two documents, and merely for purposes of example and without limitation, descriptors for the levels of E/M services may recognize seven components which may be used, in any combination, to define the levels of E/M services, namely: history, examination, medical decision making, counseling, coordination of care, nature of presenting problem, and time.

In existing systems, the E/M level for a particular patient encounter typically is selected by providing the clinical note from the patient encounter to a medical coding expert, who applies a complex set of standardized rules to the clinical note to select an appropriate E/M level, which in turn is used to determine the payment for the services rendered by the provider. The physician's and/or medical coder's judgment about the patient's condition may also be taken into account when selecting an E/M level to apply to the patient encounter. The resulting E/M level is then used to determine the payment for the services provided by the physician. Thus, existing professional fee coding techniques require a coding professional with a thorough understanding of E/M guidelines to analyze clinical documentation and to determine the level of service given to a patient by a provider of medical care.

As the description above illustrates, the process of selecting an appropriate E/M level to apply to a patient encounter is a complex, tedious, and time-consuming process, involving a combination of rules and human judgment, requiring a human medical coding expert with a thorough understanding of E/M guidelines to analyze clinical document in order to determine the level of service given to the patient by the provider.

SUMMARY

A computer system automatically generates and provides real-time feedback to a healthcare provider about a selected Evaluation and Management (E/M) level to assign to a patient encounter. The system provides the feedback while the healthcare provider is creating the clinical note that documents the patient encounter. The system may also automatically generate and suggest E/M levels to the healthcare provider for approval by the healthcare provider while the healthcare provider is creating the clinical note.

Other features and advantages of various aspects and embodiments of the present invention will become apparent from the following description and from the claims.

DETAILED DESCRIPTION

Figure 1:
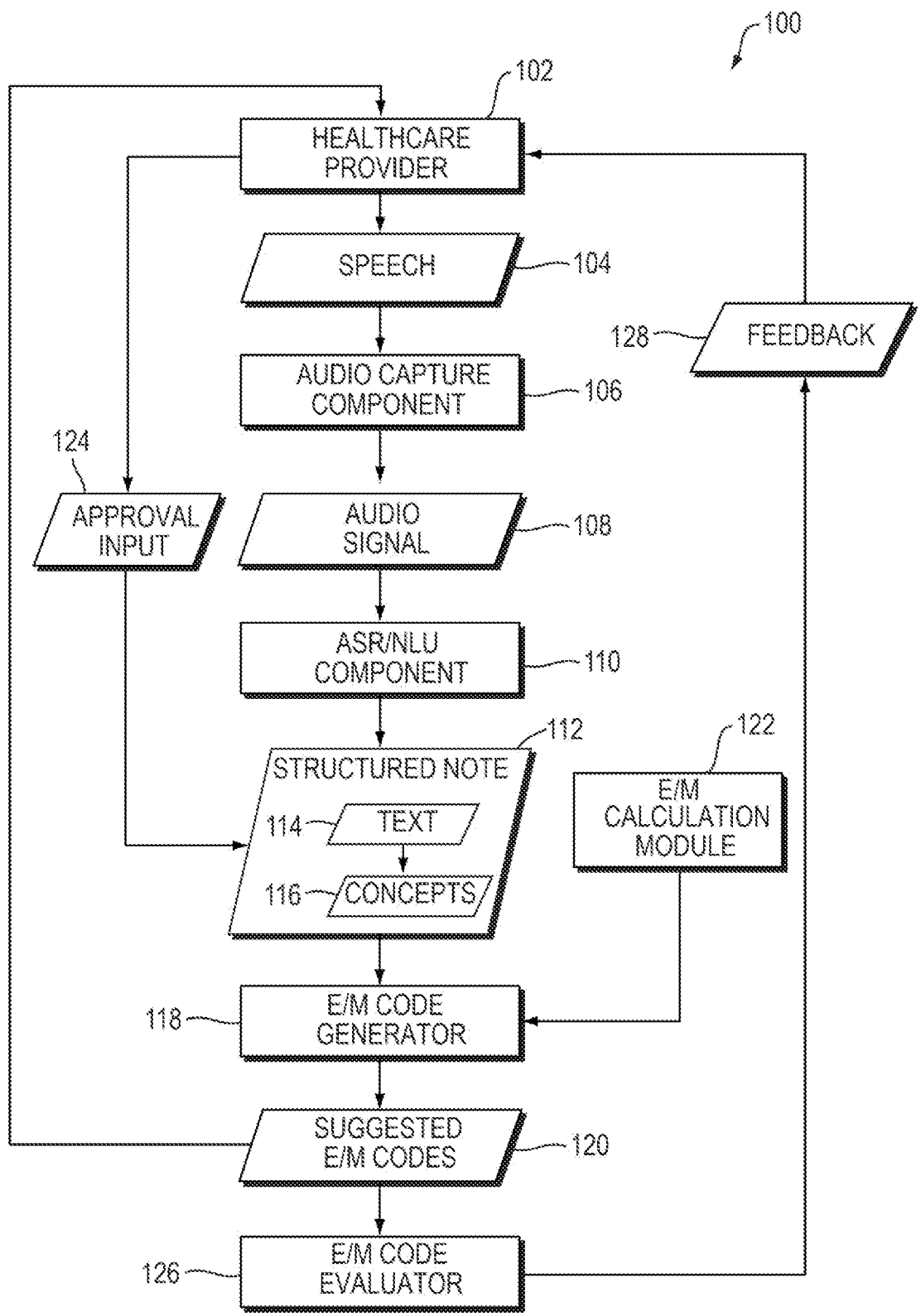
FIG. 1 is a dataflow diagram of a computer system for automatically generating providing real-time feedback to a healthcare provider about Evaluation and Management (E/M) codes selected by the healthcare provider 102 according to one embodiment of the present invention.
Figure 2:
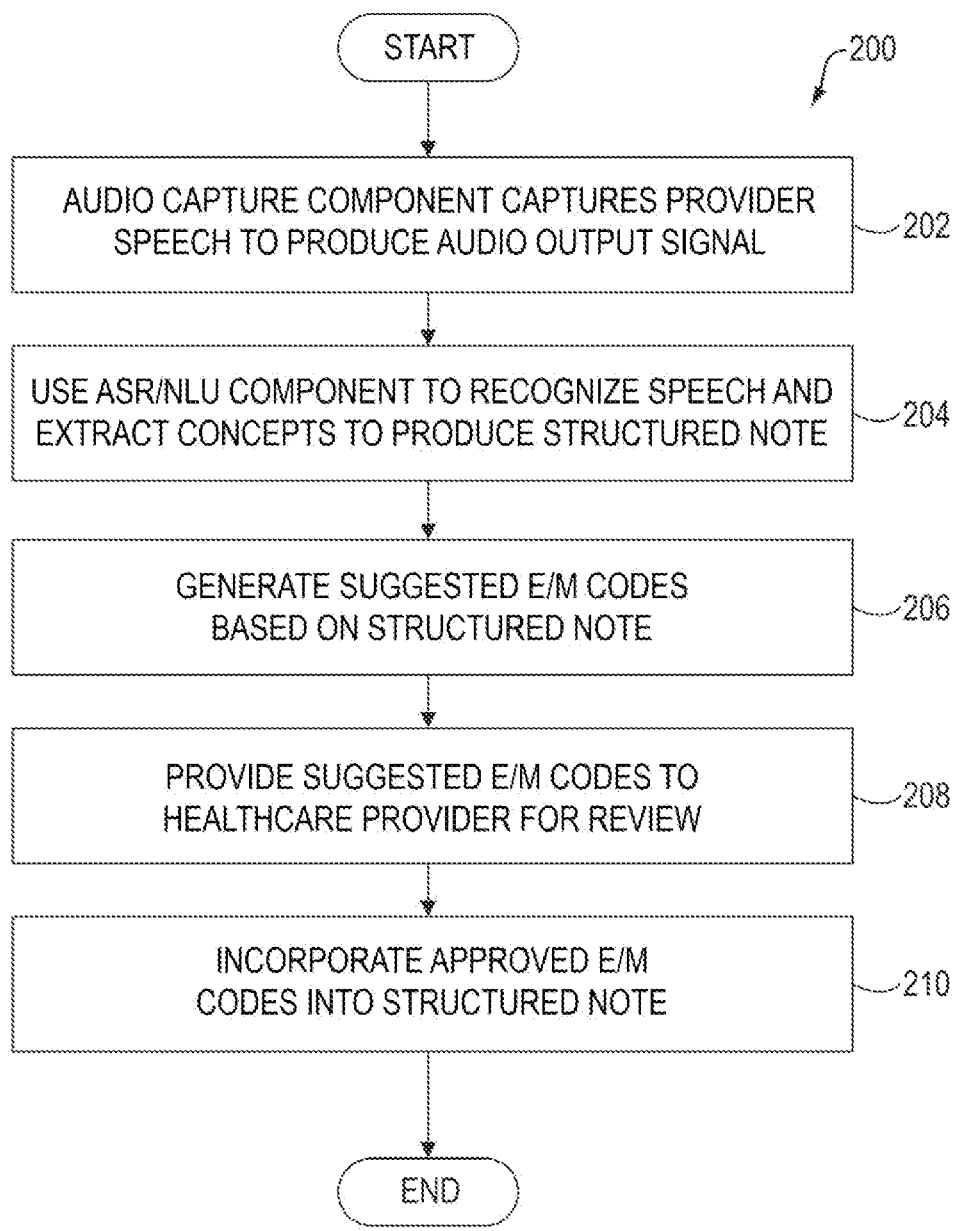
FIG. 2 is a flowchart of a method performed by the system of FIG. 1 according to one embodiment of the present invention.

Referring to FIG. 1, a dataflow diagram is shown of a computer system 100 for automatically generating providing real-time feedback to a healthcare provider 102 about Evaluation and Management (E/M) codes selected by the healthcare provider 102 according to one embodiment of the present invention. Referring to FIG. 2, a flowchart is shown of a method 200 performed by the system 100 of FIG. 1 according to one embodiment of the present invention.

An audio capture component 106 captures the speech 104 of the healthcare provider 102 (e.g., a physician) during or after a patient encounter (FIG. 2, operation 202). The healthcare provider 102 may, for example, dictate a report of the patient encounter, while the patient encounter is occurring and/or after the patient encounter is completed, in which case the speech 104 may be the speech of the healthcare provider 102 during such dictation. Embodiments of the present invention, however, are not limited to capturing speech that is directed at the audio capture component 106 or otherwise intended for use in creating documentation of the patient encounter. For example, the speech 104 may be natural speech of the healthcare provider 102 during the patient encounter, such as speech of the healthcare provider 102 that is part of a dialogue between the healthcare provider 102 and the patient. Regardless of the nature of the speech 104, the audio capture component 106 captures some or all of the speech 104 and produces, based on the speech 104, an audio output signal 108 representing some or all of the speech 104. The audio capture component 106 may use any of a variety of known techniques to produce the audio output signal 108 based on the speech 104.

Although not shown in FIG. 1, the speech 104 may include not only speech of the healthcare provider 102 but also speech of one or more additional people, such as one or more additional healthcare providers (e.g., nurses) and the patient. For example, the speech 104 may include the speech of both the healthcare provider 102 and the patient as the healthcare provider 102 engages in a dialogue with the patient as part of the patient encounter.

The audio capture component 106 may be or include any of a variety of well-known audio capture components, such as microphones, which may be standalone or integrated within or otherwise connected to another device (such as a smartphone, tablet computer, laptop computer, or desktop computer).

The system 100 also includes an automatic speech recognition (ASR) and natural language understanding (NLU) component 110, which performs automatic speech recognition and natural language processing to the audio signal 108 to produce a structured note 112, which contains both text 114 representing some or all of the words in the audio signal 108 and concepts extracted from the audio signal 108 and/or the text 114. For example, the ASR/NLU component 110 may perform automatic speech recognition and natural language processing on the audio signal 108 to produce a first portion of generated text (e.g., a first portion of the structure note 112), a first concept, and a first association between the first portion of the generated text and the first concept (FIG. 2, operation 204). The ASR/NLU 110 may, for example, perform the functions disclosed herein using any of the techniques disclosed in U.S. Pat. No. 7,584,103B2, entitled, "Automated Extraction of Semantic Content and Generation of a Structured Document from Speech" and U.S. Pat. No. 7,716,040, entitled, "Verification of Extracted Data," which are hereby incorporated by reference herein. The ASR/NLU 100 component may encode concepts in the structured note 112 using, for example, the Systematized Nomenclature of Medicine (SNOMED).

The ASR/NLU component 110 may use the structured note 112 to further identify ICD diagnoses as well as CPT procedures. The ASR/NLU component 110 may use a set of rules to identify the chief complaint (CC) and one or more E/M concepts in order to classify the subcomponents and components of the structured note 112 that make up the history, exam, and medical decision-making (MDM) sections of the E/M documentation guidelines.

The ASR/NLU component 110 may be implemented in any of a variety of ways, such as in one or more software programs installed and executing on one or more computers. Although the ASR/NLU component 110 is shown as a single component in FIG. 1 for ease of illustration, in practice the ASR/NLU component may be implemented in one or more components, such as components installed and executing on separate computers.

The structured note 112 may take any of a variety of forms, such as any one or more of the following, in any combination: a text document (e.g., word processing document), a structured document (e.g., an XML document), and a database record (e.g., a record in an Electronic Medical Record (EMR) system). Although the structured note 112 is shown as a single element in FIG. 1 for ease of illustration, in practice the structured note 112 may include one or more data structures. For example, the text 114 and the concepts 116 may be stored in distinct data structures. The structured note 112 may include data representing correspondences (e.g., links) between the text 114 and the concepts 116. For example, if the concepts 116 include a concept representing an allergy to penicillin, the structured note 112 may include data pointing to or otherwise representing text within the text 114 which represents an allergy to penicillin (e.g., "Patient has an allergy to penicillin").

The system 100 also includes an automatic Evaluation and Management (E/M) code generation module 118, which may automatically generate one or more suggested E/M codes 120 based on the structured note 112 and an E/M calculation module 122. For example, the code generation module 118 may automatically generate a first suggested E/M code based on the first portion of the generated text (e.g., the first portion of the structured note 112) and the first concept (FIG. 2, operation 206). Although the E/M code generation module 118 may generate one or more of the suggested E/M codes 120 after the structured note 112 has been generated in its entirety, this is not a limitation of the present invention. The E/M code generation module 118 may, for example, generate one or more of the suggested E/M codes 120 while the structured note 112 is being generated and before the entire structured note 112 has been generated, e.g., while any of one or more of the following is occurring:

while the healthcare provider 102 is speaking (to produce the speech 104) and before the healthcare provider 102 has produced all of the speech 104;

while the audio capture component 106 is capturing the speech and before the audio capture component 106 has captured all of the speech 104;

while the audio capture component 106 is generating the audio signal 108 and before the audio capture component 106 has generated all of the audio signal 108; and while the ASR/NLU component 110 is processing the audio signal 108 to produce the structured note 112 and before the ASR/NLU component 110 has produced all of the structured note 112.

The E/M code generator 118 may, for example, generate a first one of the suggested E/M codes 120 based on a first portion of the structured note 112 after the ASR/NLU component 110 has generated only that first portion of the structured note 112, after which the ASR/NLU component 110 may generate a second portion of the structured note 112, after which the E/M code generator 118 may generate, based on the first and second portions of the structured note 112, a second one of the suggested E/M codes 120, and so on. As these examples illustrate, the ASR/NLU component may perform automatic speech recognition and natural language processing on the audio signal 108 to produce a second portion of generated text (e.g., a second portion of the structured note 112), a second concept, and a second association between the second portion of the generated text and the second concept (FIG. 2, operation 208). Furthermore, as these examples illustrate, the code generation module 118 may automatically generate a second suggested E/M code based on the second portion of the generated text (e.g., the second portion of the structured note 112) and the second concept (FIG. 2, operation 210). As merely a few examples, the E/M code generator 118 may generate a first one of the suggested E/M codes 120 within 100 milliseconds, 200 milliseconds, 500 milliseconds, 1 second, 2 seconds, or 5 seconds of the first portion of the structured note 112 being generated. In this sense, the E/M code generator 118 may generate the suggested E/M codes 120 in real-time or near real-time.

The E/M code generation module 118 generates the suggested E/M codes 120 "automatically" in the sense that the E/M code generation module 118 generates the suggested E/M codes 120 without receiving input from the healthcare provider 102 or other user, other than by receiving data derived from the speech 104 in the form of the structured note 112. The E/M code generation module 118, in other words, receives the structured note 112 and, in response to receiving the structured note 112, generates the suggested E/M codes 120 automatically based on the structured note 112 and the E/M calculation module 122 without receiving or relying on any user input in the process of generating the suggested E/M codes 120.

The E/M calculation module 122 codifies professional fee guidelines for generating E/M codes based on clinical notes, such as the structured note 112. The E/M calculation module standardizes coding practices and improves efficiency as well as quality for coders and auditors. This includes using real-time NLU (such as by using the M*Modal Natural Language Processing (NLP) engine, available from M*Modal of Franklin, TN) to identify clinical findings in the structured note 112 while the structured note 112 is being created, in real-time or near real-time. The E/M calculation module 122 may also use as input, for example, information relating to the patient encounter, such as the length of the encounter, the duration of the audio signal 108, and the admitting diagnosis for the patient. The E/M calculation module 122 may also use as input the subcomponents and components of the structured note 112 that were previously identified, as described above.

The system 100 provides the suggested E/M codes 120 to the healthcare provider 102 for review (FIG. 2, operation 212). The system 100 may generate output representing the suggested E/M codes 120 in any of a variety of ways, such as by displaying text representing one or more of the suggested E/M codes 120. In response to being prompted by the system 100 to review the suggested E/M codes 120, the healthcare provider 102 provides input 124 indicating whether the healthcare provider 102 approves or disapproves of the suggested E/M codes 120. The system 100 receives the input 124, and may automatically incorporate any E/M codes approved by the healthcare provider 102 into the structured note 112 and not incorporate any E/M codes not approved by the healthcare provider 102 into the structured note 112 (FIG. 2, operation 214).

The approval process implemented by operations 212 and 214 may be performed in real-time or near real-time. For example, the E/M code generator 118 may provide one or more of the suggested E/M codes to the healthcare provider 102, and the healthcare provider 102 may provide the approval input 124:
- after the healthcare provider 102 has produced some of the speech 104 and before the healthcare provider 102 has produced all of the speech 104;
- while the audio capture component 106 is capturing the speech 104 and before the audio capture component 106 has captured all of the speech 104;
- while the audio capture component 106 is generating the audio signal 108 and before the audio capture component 106 has generated all of the audio signal 108;
- while the ASR/NLU component 110 is processing the audio signal 108 to produce the structured note 112 and before the ASR/NLU component 110 has produced all of the structured note 112; and
- after the E/M code generation module 118 has produced some of the E/M codes 120 and before the E/M code generation module 118 has produced all of the E/M codes 120.

As described above, the E/M code generator 118 may automatically generate suggested E/M codes 120 for review and approval by the healthcare provider 102. Additionally, or alternatively, the healthcare provider 102 may input suggested E/M codes 120 to the system 100, in response to which the system 100 may evaluate the suggested E/M codes 120 input by the healthcare provider 102 and provide feedback to the healthcare provider 102 on those suggested E/M codes 120.

In some embodiments, the system 100 automatically generates the suggested E/M codes 120 and the healthcare provider 102 reviews those codes 120 but does not manually enter any suggested E/M codes 120 to the system 100. In other embodiments, the healthcare provider 102 manually enters the suggested E/M codes 120 into the system 100 and the system 100 does not automatically generate any of the suggested E/M codes 120. In yet other embodiments, the system 100 automatically generates some of the suggested E/M codes 120 and the healthcare provider 102 manually enters some of the suggested E/M codes 120.

The healthcare provider 102 may enter some or all of the suggested E/M codes 120 at any of the times described above, such as while the structured note 112 is being generated and before the entire structured note 112 has been generated. For example, the healthcare provider 102 may dictate the structured note 112 and, after describing part of the patient encounter, provide input specifying a suggested E/M code in connection with the part of the patient encounter that was just dictated, and then continue to dictate additional parts of the structured note.

The system 100 may include an E/M code evaluator 126, which may receive the E/M codes 120 input by the healthcare provider 102 and perform any of a variety of functions on those E/M codes 120. For example, the E/M code evaluator 126 may automatically generate, and provide to the healthcare provider 102, feedback 128 on the healthcare provider 102's suggested E/M codes 120, such as recommendations to keep or change the suggested E/M codes 120 to different E/M codes 120, or to document the patient encounter more fully to match the healthcare provider 102's suggested E/M codes 120. The E/M code evaluator 126 may, for example, determine that the structured note 112 justifies assigning a higher level E/M code than one of the healthcare provider 102's suggested E/M codes 120 and, in response to that determination, recommend (via the feedback 128) that the higher level E/M code replace the healthcare provider 102's suggested E/M code. Conversely, the E/M code evaluator 126 may, for example, determine that an E/M level represented by one of the healthcare provider 102's suggested E/M codes 120 is not justified by the structured note 112 and, in response to that determination, recommend (via the feedback 128) that an E/M code having a lower level than the healthcare provider 102's suggested E/M code be used to replace the healthcare provider 102's suggested E/M code. In cases in which the system 100 recommends that the E/M level be increased, the system 100 may provide output to the healthcare provider 102 indicating the type of documentation that is needed to justify the recommended higher E/M level.

Even if the E/M code evaluator 126 determines that the suggested E/M codes 120 are not justified by the structured note 112, the E/M code evaluator 126 may not recommend that further action be taken (e.g., that the healthcare provider 102 provide additional documentation to justify the E/M codes 120 or that the E/M codes 120 be sent to a billing coding specialist for review). For example, there are many situations in which more verbose documentation would not impact the current E/M level. If the system 100 determines that one of the suggested E/M codes is not justified by the structured note 112, and also determines that providing additional documentation within the structured note 112 would not increase the level of the suggested E/M code, then the system 100 may automatically decide not to request or suggest documentation changes, because such changes would not impact the E/M level, thereby avoiding wasting the healthcare provider 102's time to add more documentation.

As another example, the E/M code evaluator 126 may automatically decide, based on the healthcare provider 102's E/M codes 120, to provide those E/M codes 120 to a billing coding specialist for review, or to recommend that the E/M codes 120 be provided to a billing coding specialist for review. For example, the E/M code evaluator 126 may automatically decide to recommend that the E/M codes 120 be provided to a billing coding specialist for review in response to determining that the structured note 112 does not justify one or more of the suggested E/M codes 120. As yet another example, the healthcare provider 102 may provide input to the system 100 indicating that the E/M code generator 118's automatically generated codes 120 should be provided to a billing coding specialist for review.

While the healthcare provider 102 is dictating the structured note 112, the system 100 may determine whether a particular aspect of the patient encounter has been documented sufficiently in the structured note 112 and, in response to determining that the particular aspect of the patient encounter has been documented sufficiently for billing purposes in the structured note 112, the system 100 may notify the healthcare provider 102 of this so that the healthcare provider 102 can stop dictating additional information about that aspect of the patient encounter and move on to other aspects of the patient encounter.

As yet another example, the system 100 may provide the healthcare provider 102 with the option to provide input indicating that the suggested E/M codes 120 should be sent to a billing coding specialist for review. In response to receiving such input (e.g., the pressing of a "Send to Coding" button by the healthcare provider 102), the system 100 may send the suggested E/M codes 120 to a billing coding specialist for review (whether the suggested E/M codes 120 were generated automatically by the system 100 or manually by the healthcare provider 102).

Embodiments of the present invention have a variety of advantages. For example, existing systems require E/M codes to be generated on the back-end, i.e., as a post-process after the healthcare provider 102 has finished speaking (i.e., producing the speech 104), and typically after the structured note 112 has been generated. Such an approach can be highly inefficient and prone to error for a variety of reasons. As just one example, if the billing coding specialist who is producing the E/M codes based on the structured note 112 has any questions about the patient encounter, that specialist typically must contact the healthcare provider 102 with questions, often long after the patient encounter has concluded. In this situation, the memory of the healthcare provider 102 may have faded and the billing coding specialist incurs a delay in generating the required E/M codes even if the healthcare provider is able to answer the billing coding specialist's questions.

In contrast, embodiments of the present invention allow the healthcare provider to review and approve of automatically-generated E/M codes 120 on the front end, i.e., at the time the structured note 112 is being created, while the healthcare provider 102's memory of the patient encounter is fresh and while the healthcare provider 102 is working on creating the structured note 112. Embodiments of the present invention do this, in part, by generating the suggested E/M codes 120 and/or the feedback 128 during the patient encounter and while the structured note 112 is being generated. As a result of such real-time code and feedback generation by the system 100, the healthcare provider 102 does not need to become involved in the E/M code generation process again at a later time, and the involvement of a separate billing coding specialist may be minimized or eliminated. Even if the healthcare provider 102 does route the structured note 112 to a billing coding specialist for review and final approval, embodiments of the present invention make it more likely that the billing coding specialist will receive all necessary information from the healthcare provider 102, because of the real-time feedback and guidance that the system 100 provides to the healthcare provider 102 at the time of creation of the structured note 112.

Real-time generation of the codes 120 and feedback 128 is not a feature that is present in prior art systems and is not performed manually by humans in existing systems. Such real-time features are only made possible by the computer-implemented techniques disclosed herein, which perform processing automatically and quickly enough to enable the codes 120 and feedback 128 to be generated in real-time, e.g., while the patient encounter is ongoing and before the creation of the structured note is complete. Embodiments of the present invention, therefore, are inherently rooted in computer technology and do not merely automate manual processes.

Another advantage of embodiments of the present invention is that they use computer technology to generate E/M codes that have higher quality than the E/M codes that are manually generated by the healthcare provider 102, and do so while the patient is still receiving treatment from the healthcare provider 102. Embodiments of the present invention may, for example, alert the healthcare provider 102 when the manually-generated E/M codes 120 are not sufficiently justified by the content of the structured note 112 in progress, thereby giving the healthcare provider 102 the opportunity to obtain additional information necessary to justify the manually-generated E/M codes 120 while the patient is still present and the patient encounter is still ongoing, whereas such an opportunity would be lost if the system 100 did not alert the healthcare provider 102 until after the patient encounter had concluded. The automatic determination by a computer that a human-generated E/M code is not sufficiently justified by the content of the structured note 112 is a step that is not present in the prior art and is not merely an automation of an otherwise manual process.

Although the description herein refers to E/M codes, this is merely an example and not a limitation of the present invention. More generally, embodiments of the present invention may be applied to other kinds of codes, such as hierarchical condition codes, critical care codes, and preventive medicine codes.

The invention can indicate to the healthcare provider that they have sufficiently documented some area of the encounter (for the purposes of billing), so that they can move on if there is no clinical need to document further.

The invention can use other data sources to determine the expected E/M level and thus provide better critiques if documentation is lower than needed for the expected E/M level (e.g., length of time the provider spent with the patient is predictive of the E/M level).

Similarly, the invention may provide the option to automatically correct the documents with missing information, not by applying a rigid "Exam Template," but by using NLU to determine an appropriate place to add the missing information and adding it automatically, or suggesting it and then adding it in response to user approval.

In real-time, while the note is being generated, the invention may tell the provider that he has sufficiently documented some area of the encounter (for the purpose of justifying an E/M code), so that the provider can move on if there is no clinical need to provide further documentation. This saves time for the provider.

The invention can use other data sources to determine the expected E/M level, and thereby provide better critiques if the documentation is lower than needed for the expected E/M level. For example, the invention may use the length of time the provider spent with the patient to identify an expected E/M level, and then ask the provider for more documentation if more documentation is needed to support the expected E/M level based on the amount of time the provider spent with the patient.

It is to be understood that although the invention has been described above in terms of particular embodiments, the foregoing embodiments are provided as illustrative only, and do not limit or define the scope of the invention. Various other embodiments, including but not limited to the following, are also within the scope of the claims. For example, elements and components described herein may be further divided into additional components or joined together to form fewer components for performing the same functions.

Any of the functions disclosed herein may be implemented using means for performing those functions. Such means include, but are not limited to, any of the components disclosed herein, such as the computer-related components described below.

The techniques described above may be implemented, for example, in hardware, one or more computer programs tangibly stored on one or more computer-readable media, firmware, or any combination thereof. The techniques described above may be implemented in one or more computer programs executing on (or executable by) a programmable computer including any combination of any number of the following: a processor, a storage medium readable and/or writable by the processor (including, for example, volatile and non-volatile memory and/or storage elements), an input device, and an output device. Program code may be applied to input entered using the input device to perform the functions described and to generate output using the output device.

Embodiments of the present invention include features which are only possible and/or feasible to implement with the use of one or more computers, computer processors, and/or other elements of a computer system. Such features are either impossible or impractical to implement mentally and/or manually. For example, embodiments of the present invention use computerized automatic speech recognition and natural language understanding components to automatically recognize and understand speech, in order to generate a structured note which contains both text and data representing concepts embodied in that text. Such components are inherently computer-implemented and provide a technical solution to the technical problem of automatically generating documents based on speech.

Any claims herein which affirmatively require a computer, a processor, a memory, or similar computer-related elements, are intended to require such elements, and should not be interpreted as if such elements are not present in or required by such claims. Such claims are not intended, and should not be interpreted, to cover methods and/or systems which lack the recited computer-related elements. For example, any method claim herein which recites that the claimed method is performed by a computer, a processor, a memory, and/or similar computer-related element, is intended to, and should only be interpreted to, encompass methods which are performed by the recited computer-related element(s). Such a method claim should not be interpreted, for example, to encompass a method that is performed mentally or by hand (e.g., using pencil and paper). Similarly, any product claim herein which recites that the claimed product includes a computer, a processor, a memory, and/or similar computer-related element, is intended to, and should only be interpreted to, encompass products which include the recited computer-related element(s). Such a product claim should not be interpreted, for example, to encompass a product that does not include the recited computer-related element(s).

Each computer program within the scope of the claims below may be implemented in any programming language, such as assembly language, machine language, a high-level procedural programming language, or an object-oriented programming language. The programming language may, for example, be a compiled or interpreted programming language.

Each such computer program may be implemented in a computer program product tangibly embodied in a machine-readable storage device for execution by a computer processor. Method steps of the invention may be performed by one or more computer processors executing a program tangibly embodied on a computer-readable medium to perform functions of the invention by operating on input and generating output. Suitable processors include, by way of example, both general and special purpose microprocessors. Generally, the processor receives (reads) instructions and data from a memory (such as a read-only memory and/or a random access memory) and writes (stores) instructions and data to the memory. Storage devices suitable for tangibly embodying computer program instructions and data include, for example, all forms of non-volatile memory, such as semiconductor memory devices, including EPROM, EEPROM, and flash memory devices; magnetic disks such as internal hard disks and removable disks; magneto-optical disks; and CD-ROMs. Any of the foregoing may be supplemented by, or incorporated in, specially-designed ASICs (application-specific integrated circuits) or FPGAs (Field-Programmable Gate Arrays). A computer can generally also receive (read) programs and data from, and write (store) programs and data to, a non-transitory computer-readable storage medium such as an internal disk (not shown) or a removable disk. These elements will also be found in a conventional desktop or workstation computer as well as other computers suitable for executing computer programs implementing the methods described herein, which may be used in conjunction with any digital print engine or marking engine, display monitor, or other raster output device capable of producing color or gray scale pixels on paper, film, display screen, or other output medium.

Any data disclosed herein may be implemented, for example, in one or more data structures tangibly stored on a non-transitory computer-readable medium. Embodiments of the invention may store such data in such data structure(s) and read such data from such data structure(s).

The invention claimed is:

1. A method performed by at least one computer processor executing computer program instructions stored on at least one non-transitory computer-readable medium, the method comprising:
   (1) at an audio capture component:
      (1)(a) capturing a first portion of speech of a healthcare provider and a first portion of speech of a patient;
      (1)(b) producing a first audio signal representing the first portion of speech of the healthcare provider and the first portion of speech of the patient;
   (2) at an automatic speech recognition/natural language understanding (ASR/NLU) component, generating, based on the first audio signal, a first data structure containing: (a) first text, within a document, the first text representing first speech of the healthcare provider and first speech of the patient; (b) a first concept; and (c) a first association between the first text and the first concept;
   (3) in real-time, and before the healthcare provider has produced all of the speech as part of a healthcare provider/patient encounter, at a medical code generator module:
      (3)(a) generating a first medical code automatically based on the first text and the first concept; and
      (3)(b) incorporating the first medical code into the document;
   (4) at the audio capture component:
      (4)(a) capturing a second portion of speech of the healthcare provider and a second portion of speech of the patient;
      (4)(b) producing a second audio signal representing the second portion of speech of the healthcare provider and the second portion of speech of the patient;
   (5) at the automatic speech recognition/natural language understanding (ASR/NLU) component, generating, based on the second audio signal, a second data structure containing: (a) second text, within the document, the second text representing second speech of the healthcare provider and second speech of the patient; (b) a second concept; and (c) a second association between the second text and the second concept; and
   (6) at the medical code generator module:
      (6)(a) generating a second medical code automatically based on the second text and the second concept; and
      (6)(b) incorporating the second medical code into the document.

2. The method of claim 1, wherein the first and second medical codes comprises at least one of a hierarchical condition code, critical care code, preventive medicine code, and an evaluation and management (E/M) code.

3. The method of claim 1, further comprising:
   determining, in real-time, whether at least one of the first medical code and the second medical code sufficiently documents an aspect of the healthcare provider/patient encounter; and
   when it is determined that at least one of the first medical code and second medical code is sufficient to document the aspect of the healthcare provider/patient encounter, automatically generating an indication that is presented to the healthcare provider that there is no clinical need to provide further documentation.

4. The method of claim 1, further comprising:
   receiving a code from the healthcare provider prior to completion of a healthcare provider/patient encounter;
   determining, in real-time and based at least in part on one of the first medical code and the second medical code, whether the received code is sufficiently documented by any aspect of the healthcare provider/patient encounter; and
   when it is determined that the received code is not sufficiently documented by any aspect of the healthcare provider/patient encounter, automatically generating an indication that is presented to the healthcare provider that there is not sufficient information to justify the received code.

5. The method of claim 4, where the indication further comprises at least one of a prompt requesting additional information; a prompting suggesting that the level of the received code be lowered, and a prompting requesting whether the received code should be routed for final review and approval.

6. The method of claim 3 or 4, wherein the first and second medical codes are E/M codes and further comprising:
   determining a length of the healthcare provider/patient encounter; and
   modifying at least one of the first medical code or the second medical code to generate an expected E/M code based on the length of the encounter.

7. A non-transitory computer-readable medium comprising computer program instructions executable by at least one computer processor to perform a method, the method comprising:
   (1) at an audio capture component:
      (1)(a) capturing a first portion of speech of a healthcare provider and a first portion of speech of a patient;
      (1)(b) producing a first audio signal representing the first portion of speech of the healthcare provider and the first portion of speech of the patient;
   (2) at an automatic speech recognition/natural language understanding (ASR/NLU) component, generating, based on the first audio signal, a first data structure containing: (a) first text, within a document, the first text representing first speech of the healthcare provider and first speech of the patient; (b) a first concept; and (c) a first association between the first text and the first concept;
   (3) in real-time, and before the healthcare provider has produced all of the speech as part of a healthcare provider/patient encounter, at a medical code generator module:
      (3)(a) generating a first medical code automatically based on the first text and the first concept; and
      (3)(b) incorporating the first medical code into the document;
   (4) at the audio capture component:
      (4)(a) capturing a second portion of speech of the healthcare provider and a second portion of speech of the patient;
      (4)(b) producing a second audio signal representing the second portion of speech of the healthcare provider and the second portion of speech of the patient;
   (5) at the automatic speech recognition/natural language understanding (ASR/NLU) component, generating, based on the second audio signal, a second data structure containing: (a) second text, within the document, the second text representing second speech of the healthcare provider and second speech of the patient; (b) a second concept; and (c) a second association between the second text and the second concept; and (6) at the medical code generator module:
(6)(a) generating a second medical code automatically based on the second text and the second concept; and
(6)(b) incorporating the second medical code into the document.

8. The method of claim 7, wherein the first and second medical codes comprises at least one of a hierarchical condition code, critical care code, preventive medicine code, and an evaluation and management (E/M) code.

9. The method of claim 7, further comprising:
determining, in real-time, whether at least one of the first medical code and the second medical code sufficiently documents an aspect of the healthcare provider/patient encounter; and
when it is determined that at least one of the first medical code and second medical code is sufficient to document the aspect of the healthcare provider/patient encounter, automatically generating an indication that is presented to the healthcare provider that there is no clinical need to provide further documentation.

10. The method of claim 7, further comprising:
receiving a code from the healthcare provider prior to completion of a healthcare provider/patient encounter;
determining, in real-time and based at least in part on one of the first medical code and the second medical code, whether the received code is sufficiently documented by any aspect of the healthcare provider/patient encounter; and
when it is determined that the received code is not sufficiently documented by any aspect of the healthcare provider/patient encounter, automatically generating an indication that is presented to the healthcare provider that there is not sufficient information to justify the received code.

11. The method of claim 10, where the indication further comprises at least one of a prompt requesting additional information; a prompting suggesting that the level of the received code be lowered, and a prompting requesting whether the received code should be routed for final review and approval.

12. The method of claim 9 or 10, wherein the first and second medical codes are E/M codes and further comprising:
determining a length of the healthcare provider/patient encounter; and
modifying at least one of the first medical code or the second medical code to generate an expected E/M code based on the length of the encounter.

13. A computer system comprising:
one or more computer processors;
one or more display devices communicatively coupled to the one or more processors;
an audio capture component;
an automatic speech recognition/natural language understanding (ASR/NLU) component;
a medical code generator module;
a non-transitory computer-readable medium, communicatively coupled to the one or more processors, comprising computer program instructions executable by the one or more computer processors to perform a method, the method comprising:

(1) at the audio capture component:
(1)(a) capturing a first portion of speech of a healthcare provider and a first portion of speech of a patient;
(1)(b) producing a first audio signal representing the first portion of speech of the healthcare provider and the first portion of speech of the patient;
(2) at the automatic speech recognition/natural language understanding (ASR/NLU) component, generating, based on the first audio signal, a first data structure containing: (a) first text, within a document, the first text representing first speech of the healthcare provider and first speech of the patient; (b) a first concept; and (c) a first association between the first text and the first concept;
(3) in real-time, and before the healthcare provider has produced all of the speech as part of a healthcare provider/patient encounter, at the medical code generator module:
(3)(a) generating a first medical code automatically based on the first text and the first concept; and
(3)(b) incorporating the first medical code into the document;
(4) at the audio capture component:
(4)(a) capturing a second portion of speech of the healthcare provider and a second portion of speech of the patient;
(4)(b) producing a second audio signal representing the second portion of speech of the healthcare provider and the second portion of speech of the patient;
(5) at the automatic speech recognition/natural language understanding (ASR/NLU) component, generating, based on the second audio signal, a second data structure containing: (a) second text, within the document, the second text representing second speech of the healthcare provider and second speech of the patient; (b) a second concept; and (c) a second association between the second text and the second concept; and
(6) at the medical code generator module:
(6)(a) generating a second medical code automatically based on the second text and the second concept; and
(6)(b) incorporating the second medical code into the document.

14. The computer system of claim 13, wherein the first and second medical codes comprises at least one of a hierarchical condition code, critical care code, preventive medicine code, and an evaluation and management (E/M) code.

15. The computer system of claim 13, wherein the method further comprises:
determining, in real-time, whether at least one of the first medical code and the second medical code sufficiently documents an aspect of the healthcare provider/patient encounter; and
when it is determined that at least one of the first medical code and second medical code is sufficient to document the aspect of the healthcare provider/patient encounter, automatically generating an indication on the one or more display devices that is presented to the healthcare provider that there is no clinical need to provide further documentation.

16. The computer system of claim 13, wherein the method further comprises:
receiving a code from the healthcare provider prior to completion of a healthcare provider/patient encounter;

determining, in real-time and based at least in part on one of the first medical code and the second medical code, whether the received code is sufficiently documented by any aspect of the healthcare provider/patient encounter; and when it is determined that the received code is not sufficiently documented by any aspect of the healthcare provider/patient encounter, automatically generating an indication on the one or more display devices that is presented to the healthcare provider that there is not sufficient information to justify the received code.

17. The method of claim 16, wherein the indication further comprises at least one of a prompt requesting additional information; a prompting suggesting that the level of the received code be lowered, and a prompting requesting whether the received code should be routed for final review and approval.

* * * * *